United States Patent [19]

Miller et al.

[11] 4,093,655
[45] June 6, 1978

[54] AMIDINE RICE HERBICIDES

[75] Inventors: George A. Miller, Glenside; Marvin H. Fleischfresser, Warrington, both of Pa.

[73] Assignee: Rohm and Haas Company, Philadelphia, Pa.

[21] Appl. No.: 28,038

[22] Filed: Apr. 13, 1970

[51] Int. Cl.² .......................................... C07C 123/00
[52] U.S. Cl. ............................... 260/564 RF; 71/121
[58] Field of Search .................... 260/564 R, 564 RF

[56] References Cited

U.S. PATENT DOCUMENTS

| | | | |
|---|---|---|---|
| 3,119,831 | 1/1964 | Homer | 260/296 |
| 3,189,648 | 6/1965 | Gerjovich | 260/564 |
| 3,218,147 | 11/1965 | Homer | 71/2.3 |
| 3,462,537 | 8/1969 | Merk | 42/326 X |
| 3,557,128 | 1/1971 | Pallos | 260/294.9 |

FOREIGN PATENT DOCUMENTS 964,640  7/1964  United Kingdom ................ 260/564

*Primary Examiner*—Gerald A. Schwartz

[57] ABSTRACT

Weeds in rice are controlled by applying amidines of the formula

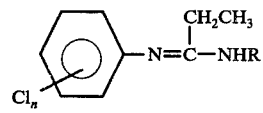

wherein R is a $(C_4-C_{12})$alkyl group, and
$n$ is 1 to 3.

The amidines and herbicidal compositions containing them are useful for the control of weeds in both direct-seeded and transplanted rice.

6 Claims, No Drawings

AMIDINE RICE HERBICIDES

This invention relates to compositions and methods for controlling the growth of weeds in rice.

Because rice is one of the world's most important cereal grain crops, there has been a continuing search for improved herbicides for controlling the growth of weeds in rice crops. A useful rice herbicide should kill the unwanted weeds without causing undue injury to the rice plants and should give lasting weed control at low dosages. Since all the known rice herbicides fall short of perfection, it would be desirable to have new rice herbicides which have improved features or which will complement the known rice herbicides in activity.

It has now been found that weeds in rice are controlled by applying novel amidine compounds of the formula

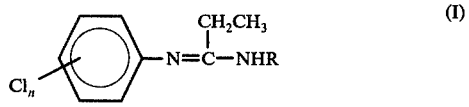

wherein R is a $(C_4-C_{12})$alkyl group, and
n is 1 to 3, preferably 1 or 2.

The chlorine atoms can be arranged in any of the possible isomeric relationships around the phenyl ring. For example,
when n is one, the chlorine atom can be ortho, meta, or para to the amidine group, when n is two, the 2,3-, 2,4-, 2,5-, 2,6-, 3,4-, and 3,5-dichloro isomers are included, and when n is three, the 2,3,4-, 2,3,5-, 2,3,6-, 2,4,5-, 2,4,6-, and 3,4,5-trichloro isomers are comprehended. R can have either a straight- or branched-chain or cyclic spatial configuration. In a preferred embodiment of the invention, R is a $(C_6-C_{10})$alkyl group.

Examples of the amidine compounds of the invention which are useful as selective rice herbicides include:
N-butyl-N'-(3,4-dichlorophenyl)propionamidine,
N-pentyl-N'-(3,4-dichlorophenyl)propionamidine,
N-hexyl-N'-(3-chlorophenyl)propionamidine,
N-hexyl-N'-(4-chlorophenyl)propionamidine,
N-hexyl-N'-(3,4-dichlorophenyl)propionamidine,
N-hexyl-N'-(3,4,5-trichlorophenyl)propionamidine,
N-heptyl-N'-(2-chlorophenyl)propionamidine,
N-octyl-N'-(2,3,4-trichlorophenyl)propionamidine,
N-octyl-N'-(2,3-dichlorophenyl)propionamidine,
N-octyl-N'-(3,4-dichlorophenyl)propionamidine,
N-octyl-N'-(2-chlorophenyl)propionamidine,
N-octyl-N'-(3-chlorophenyl)propionamidine,
N-octyl-N'-(4-chlorophenyl)propionamidine,
N-nonyl-N'-(3,4-dichlorophenyl)propionamidine,
N-nonyl-N'-(2,4-dichlorophenyl)propionamidine,
N-decyl-N'-(3,4-dichlorophenyl)propionamidine,
N-decyl-N'-(3,5-dichlorophenyl)propionamidine,
N-decyl-N'-(2,4,5-trichlorophenyl)propionamidine,
N-undecyl-N'-(2,6-dichlorophenyl)propionamidine,
N-dodecyl-N'-(3,4-dichlorophenyl)propionamidine,
and the like.

The amidines of the invention are useful as selective herbicides both in direct-seeded rice and in transplanted rice. When used in direct-seeded rice crops, the amidines are applied postemergence as to both the rice and the weeds — that is, they are applied to the plants during early stages of growth while they are in a tender state and will selectively control the growth of the weed plants. When used in transplanted rice crops, the amidines can be applied either preemergence or postemergence as to the weeds — that is, they can be applied to the transplanted rice plants and their growth medium either before the weed plants emerge or while the weed plants are in their early stages of growth. The amidines can be applied to the growth medium either before or after the rice has been transplanted to that medium. When used in paddy rice crops, the amidines are usually applied directly on the flooded rice field.

The amidines of the invention exhibit three unexpected advantageous properties. Firstly, the amidines of the invention show greater postemergence activity in a water environment than in dry-land applications. Secondly, the amidines of the invention have good preemergence activity in a water environment, but show very little or no preemergence activity in dry-land applications at reasonable application rates. Thirdly, the amidines of the invention are much more stable chemically and less subject to hydrolysis in a water environment than the related formamidines, thus suggesting greater activity and more residual control of weeds for the amidines of the invention. The possession of these properties by the amidines of the invention makes them particularly useful as selective rice herbicides.

The amidines of the invention can be applied to the growth medium or to the rice crop in any amount which will give the required control of weeds. Generally, the rate of application is from about one-half to about 20 pounds of the amidine per acre, and preferably from about 2 to about 8 pounds of the amidine per acre.

An amidine of the invention can be applied to the growth medium or to plants to be treated either by itself or, as is generally done, as a component in a herbicidal composition or formulation which also comprises an agronomically acceptable carrier. By agronomically acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the amidines of the invention may also be used in any of these herbicidal formulations. The herbicidal compositions of the invention can be either solid or liquid formulations or solutions. For example, the amidines can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers 1969 Annual."

The amidine compounds of this invention can be dissolved in any appropriate solvent. Examples of solvents which are useful in the practice of this invention include alcohols, ketones, aromatic hydrocarbons, dimethylformamide, dioxane, dimethyl sulfoxide, and the like. Mixtures of these solvents can also be used. The concentration of the solution can vary from about 2% to about 98% with a preferred range being about 25% to about 75%.

For the preparation of emulsifiable concentrates, the amidine can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to about 50% and in flowable emulsion concentrates, this can be as high as about 75%.

Wettable powders suitable for spraying can be prepared by admixing the amidine with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent can constitute about 0.5% to about 3% of the composition, and a wetting agent can constitute from about 0.1% to about 5% of the composition.

Dusts can be prepared by mixing the amidines of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating a solid such as granular fuller's earth, vermiculite, ground corn cobs, seed hulls, including bran or other grain hulls, or similar material. A solution of one or more of the amidines in a volatile organic solvent can be sprayed or mixed with the granular solid and the solvent then removed by evaporation. The granular material can have any suitable size, with a preferable size range of 16 to 60 mesh. The amidine will usually comprise about 2 to 15% of the granular formulation.

The amidines of the invention can also be mixed with fertilizers or fertilizing materials before their application. In one type of solid fertilizing composition in which the amidines can be used, particles of a fertilizer of fertilizing ingredients, such as ammonium sulfate, ammonium nitrate, or ammonium phosphate, can be coated with one or more of the amidines. The solid amidines and solid fertilizing material can also be admixed in mixing or blending equipment, or they can be incorporated with fertilizers in granular formulations. Any relative proportion of amidine and fertilizer can be used which is suitable for the crops and weeds to be treated. The amidine will commonly be from about 5% to about 25% of the fertilizing composition. These compositions provide fertilizing materials which promote the rapid growth of desired plants, and at the same time control the growth of undesired plants.

The amidines of the invention can be applied as herbicidal sprays by methods commonly employed, such as conventional high-gallonage hydraulic sprays, low gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with amidines of the invention. For example, herbicides which are effective against broad-leaved weeds can be used to complement or improve the activity of the herbicidal composition against such weeds. Examples of other selective rice herbicides which can be incorporated to provide additional advantages and effectiveness include:

CARBOXYLIC ACIDS AND DERIVATIVES 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salts and esters
4-(2,4-dichlorophenoxy)butyric acid and its salts and esters
4-(2-methyl-4-chlorophenoxy)butyric acid and its salts and esters
2,3,6-trichlorophenylacetic acid and its salts
3,6-endoxohexahydrophthalic acid
dimethyl 2,3,5,6-tetrachloroterephthalate
trichloroacetic acid and its salts
2,2-dichloropropionic acid and its salts
2,3-dichloroisobutyric acid and its salts

CARBAMIC ACID DERIVATIVES ethyl N,N-di(n-propyl)thiolcarbamate
propyl N,N-di(n-propyl)thiolcarbamate
ethyl N-ethyl-N-(n-butyl)thiolcarbamate
propyl N-ethyl-N-(n-butyl)thiolcarbamate
2-chloroallyl N,N-diethyldithiocarbamate
N-methyldithiocarbamic acid salts
S-ethyl hexahydro-1H-azepine-1-carbothioate
isopropyl N-phenylcarbamate
isopropyl N-(m-chlorophenyl)carbamate
4-chloro-2-butynyl N-(m-chlorophenyl)carbamate
methyl N-(3,4-dichlorophenyl)carbamate

PHENOLS dinitro-o-(sec-butyl)phenol and its salts
pentachlorophenol and its salts

DIPHENYL ETHER DERIVATIVES 2,4-dichloro-4'-nitrodiphenyl ether
2,4,6-trichloro-4'-nitrodiphenyl ether
2,4-dichloro-6-fluoro-4'-nitrodiphenyl ether 3-methyl-4'-nitrodiphenyl ether
3,5-dimethyl-4'-nitrodiphenyl ether
2,4'-dinitro-4-trifluoromethyldiphenyl ether

OTHER ORGANIC HERBICIDES

N-(3,4-dichlorophenyl)propionamide
When mixtures of herbicides are employed, the relative proportions which are used will depend upon the weeds to be treated and the degree of selectivity in weed control which is desired.

All of the amidines of the invention can be prepared from the corresponding aniline, by reacting the mono-, di-, or trichloro aniline with a trialkylorthopropionate, such as triethylorthopropionate, to form an imidate intermediate, and subsequently reacting the imidate with a primary alkyl amine to form the amidine. Various other known synthetic methods for preparing substituted amidines can also be employed. For example, an N-alkylpropionamide can be reacted with phosphorus pentachloride to form the chloroimine hydrochloride, which is subsequently reacted with a substituted aniline to form the amidine.

The following examples will further illustrate this invention but are not intended to limit it in any way.

distilled off as formed (3½ hrs.). The sample was then distilled at reduced pressure (0.15 mm Hg) and the fraction boiling at 63°–66° C. (0.9 part) was collected and identified as ethyl N-(3-chlorophenyl)propionimidate.

Ethyl N-(3-chlorophenyl)propionimidate (1 part), n-octyl-amine (1 part), and a catalytic amount of p-toluenesulfonic acid monohydrate were charged to a flask fitted with a condenser and drying tube (CaSO$_4$) and the mixture was refluxed for 15 hours, after which the flask was fitted with a 10 cm Vigreaux column and the ethanol that had formed (0.8 part) distilled off slowly (3 hours). The reaction mixture was then distilled at reduced pressure (0.15 mm Hg) to give N-n-octyl-N'-(3-chlorophenyl)propionamidine (0.7 part). The fraction boiling at 167.5° – 169° C. was collected and analyzed.

Anal. Calcd. for $C_{17}H_{27}ClN_2$: C, 68.92; H, 9.32; Cl, 12.14; N, 9.59. Found: C, 69.05; H, 9.33; Cl, 12.10; N, 9.39.

EXAMPLES 2–9

Following the procedure of Example 1, the amidines listed in Table I were prepared, by reacting the appropriate substituted aniline with the appropriate n-alkylamine.

TABLE I $$\underset{Ar-N=C-NHR}{\overset{CH_2CH_3}{|}}$$

| EX. NO. | Amidine | Ar | R | BOILING POINT °C/mm Hg | ELEMENTAL ANALYSIS (Theoretical Value in Brackets) | | | |
|---|---|---|---|---|---|---|---|---|
| | | | | | C | H | N | Cl |
| 2 | N-n-butyl-N'-(3,4-dichloro-phenyl)propionamidine | 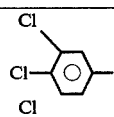 | —C$_4$H$_9$-n | — | 57.01 (57.2) | 6.88 (6.65) | 10.16 (10.25) | 25.8 (26.0) |
| 3* | N-n-octyl-N'(3,4-dichloro-phenyl)propionamidine | 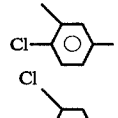 | —C$_8$H$_{17}$-n | 199/1.0 | 47.32 (47.51) | 6.51 (6.33) | 6.45 (6.52) | 24.72 (24.75) |
| 4 | N-n-dodecyl-N'-(3,4-dichloro-phenyl)propionamidine | 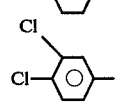 | —C$_{12}$H$_{25}$-n | 220–221/0.45 | — | — | — | — |
| 5 | N-n-hexyl-N'-(3,4-dichloro-phenyl)propionamidine | 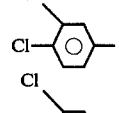 | —C$_6$H$_{13}$-n | 163–165/0.35 | 59.82 (59.9) | 7.41 (7.36) | 9.29 (9.31) | 23.19 (23.5) |
| 6* | N-n-decyl-N'-(3,4-dichloro-phenylpropionamidine | 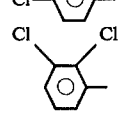 | —C$_{10}$H$_{21}$-n | 180–182/0.50 | 49.77 (49.84) | 7.07 (6.83) | 5.86 (6.12) | 23.18 (23.23) |
| 7 | N-n-nonyl-N'-(3,4-dichloro-phenyl)propionamidine | 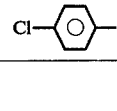 | —C$_9$H$_{19}$-n | 184–184.5/0.75 | 63.16 (62.96) | 8.19 (8.22) | 8.10 (8.16) | 20.83 (20.65) |
| 8 | N-n-octyl-N'-(3,4-dichloro-phenyl)propionamidine | 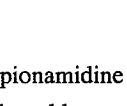 | —C$_8$H$_{17}$-n | 165–175/0.20) | — | — | — | — |
| 9 | N-n-octyl-N'-(4'-chloro-phenyl)propionamidine | 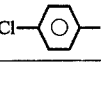 | —C$_8$H$_{17}$-n | 156–158/0.15 | 68.66 (68.92) | 9.21 (9.32) | 9.50 (9.59) | 12.17 (12.14) |

*Elemental analysis of the perchlorate salt

EXAMPLE 1

Preparation of N-n-octyl-N'-(3-chlorophenyl)propionamidine

Triethylorthopropionate (1 part) and m-chloroaniline (1 part) were charged to flask equipped with a condenser and drying tube (CaSO$_4$) and the mixture was refluxed for 20 hours. The flask was then fitted with a 10 cm Vigreaux column and the ethanol (1.8 part) was

EXAMPLE 10

Preparation of N-n-octyl-N'-(2-chlorophenyl)propionamidine n-Octylpropionamide (1 part) was added rapidly to a slurry of phosphorus pentachloride (1.5 parts) in benzene (12 parts) in a flask fitted with an addition funnel, a condenser, and a drying tube (CaSO$_4$) at room temperature (slight exotherm). After stirring for 5 minutes the mixture was warmed to reflux (1 hr.), cooled by an ice bath, and o-chloroaniline (1 part) was added dropwise with cooling (10 min.) after which the reaction mixture was refluxed for 1 hour. The reaction mixture was then cooled (ice bath) and the phosphorus oxychloride formed was hydrolyzed by addition of water (85 parts) and adjustment of the pH to 8 with concentrated ammonium hydroxide. The upper organic layer was separated and dried with anhydrous sodium sulfate to give, after removal of benzene in vacuo, a yellow oil (1 part). This oil was distilled at reduced pressure (0.15 mm Hg) ad the fraction boiling at 153.5° -154.5° C. collected. The product was found to be N-n-octyl-N'-(2-chlorophenyl)propionamidine.

EXAMPLE 11

Evaluaton of Amidines as Selective Rice Herbicides

This example shows the selective postemergence herbicidal activity in rice (Oryza sativa) of the amidines of the invention. The amidines were used against the following weeds:

| | |
|---|---|
| barnyardgrass | (*Echinocloa crusgalli*) |
| sprangletop | (*Leptochloa imbricata*) |
| coffeeweed | (*Sesbania macrocarpa*) |
| umbrella sedge | (*Cyperus difformis*) |
| redstem | (*Ammania coccinea*) |
| groundcherry | (*Physalis longifolia*) |
| canarygrass | (*Phalaris canariensis*) |
| Dallisgrass | (*Paspalus dilatatum*) |
| cattail | (*Typha latifolia*) |

The amidines of Examples 1 to 10 were evaluated.

PADDY TEST

Plants in three-inch deep pots which are 2 weeks (14 days) old and 1 week (7 days) old for postemergence applications and newly planted for preemergence applications were put into a 22-inch square metal pan which was then filled with water to 3 inches above the soil surface of the pots. A sufficient quantity of the test compound was dissolved in 100 ml. of 50% acetone to make the desired application rate in pounds per acre and poured over the water surface. Observations were made two weeks after applications.

Table II summarizes the results of these tests.

TABLE II

WEED CONTROL AND RICE INJURY IN PADDY TEST (% KILL)

| Amidine Example No. | rate (lb/A) | Preemergence | | | Postemergence 14 days old at treatment | | | | | | | | Postemergence 7 days old at treatment | | | |
|---|---|---|---|---|---|---|---|---|---|---|---|---|---|---|---|---|
| | | barnyardgrass | coffeeweed | rice | barnyardgrass | redstem | sprangletop | groundcherry | coffeeweed | canarygrass | Dallisgrass | cattail | rice | barnyardgrass | umbrella sedge | coffeeweed |
| 1 | 2 | 100 | 100 | 0 | 100 | 0 | 80 | 100 | 100 | 90 | 100 | 70 | 90 | 90 | 90 | 100 |
| 1 | 4 | 100 | 100 | 10 | 100 | 0 | 90 | 100 | 100 | 100 | 100 | 50 | 90 | 100 | 100 | 100 |
| 2 | 2 | 30 | 20 | 0 | 30 | 0 | 0 | 0 | 20 | 0 | 0 | 10 | 0 | 0 | 0 | 0 |
| 2 | 4 | 60 | 50 | 0 | 40 | 0 | 20 | 0 | 20 | 0 | 30 | 40 | 0 | 0 | 0 | 20 |
| 3 | 2* | 75 | 100 | 25 | 100 | 25 | 90 | 100 | 100 | 100 | 95 | 45 | 65 | 90 | 65 | 100 |
| 3 | 4* | 100 | 100 | 0 | 100 | 60 | 100 | 100 | 100 | 100 | 100 | 75 | 95 | 100 | 95 | 100 |
| 4 | 2 | 0 | 0 | 0 | 50 | 0 | 30 | 80 | 20 | 40 | 0 | 0 | 0 | 30 | 0 | 0 |
| 4 | 4 | 20 | 70 | 0 | 60 | 0 | 30 | 80 | 60 | 30 | 70 | 50 | 0 | 50 | 0 | 30 |
| 5 | 2 | 80 | 70 | 0 | 80 | 0 | 40 | 50 | 50 | 90 | 100 | 60 | 0 | 60 | 20 | 90 |
| 5 | 4 | 90 | 95 | 0 | 100 | 70 | 60 | 100 | 90 | 70 | 100 | 90 | 0 | 80 | 100 | 100 |
| 6 | 2 | 100 | 100 | 10 | 100 | 90 | 100 | 100 | 100 | — | 100 | 50 | 100 | 95 | 100 | 100 |
| 6 | 4 | 70 | 100 | 0 | 100 | 50 | 90 | 100 | 100 | 100 | 70 | 70 | 80 | 100 | 70 | 90 |
| 7 | 2 | 100 | 100 | 10 | 100 | 80 | 50 | 80 | 100 | — | 100 | 60 | 20 | 90 | 95 | 100 |
| 7 | 4 | 90 | 100 | 0 | 100 | 60 | 90 | 100 | 90 | — | 100 | 40 | 60 | 100 | 80 | 100 |
| 8 | 2 | 100 | 100 | 10 | 100 | 80 | 80 | 100 | 100 | 100 | 100 | 70 | 30 | 90 | 90 | 100 |
| 8 | 4 | 90 | 100 | 0 | 100 | 80 | 100 | 100 | 100 | 100 | 100 | 50 | 90 | 100 | 80 | 100 |
| 9 | 2 | 100 | 100 | 0 | 100 | 0 | 80 | 100 | 100 | 100 | 100 | 70 | 100 | 100 | 100 | 100 |
| 9 | 4 | 80 | 100 | 0 | 100 | 0 | 100 | 100 | 100 | 100 | 100 | 0 | 50 | 80 | 70 | 100 |
| 10 | 2 | 80 | 100 | 0 | 100 | 0 | 50 | 90 | 100 | 90 | 100 | 50 | 50 | 80 | 70 | 100 |
| 10 | 4 | 100 | 100 | 10 | 100 | 0 | 100 | 100 | 100 | 100 | 100 | 100 | 100 | 100 | 100 | 100 |

*average of two tests

The above tests and data indicate the selective postemergence herbicidal activity in rice of the amidines of the invention, as well as their usefulness as selective herbicides when applied preemergence as to weeds in transplanted rice.

In the above Examples 1–11, all parts are parts by weight, unless otherwise noted.

It is to be understood that changes and variations may be made without departing from the spirit and scope of the invention as defined by the appended claims.

We claim:

1. A compound of the formula

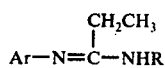

wherein R is a ($C_6$–$C_{10}$)alkyl group, and Ar is a group of the formula

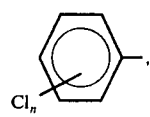

wherein $n$ is 1 to 3.

2. The compound of claim 1 wherein $n$ is 1 or 2.
3. The compound of claim 1 wherein R is a n-octyl group.
4. The compound of claim 1 wherein Ar is a 3,4-dichlorophenyl group or a 3-chlorophenyl group.
5. The compound of claim 1 wherein R is a n-octyl group and Ar is a 3,4-dichlorophenyl group.
6. N-hexyl-N'-(3,4-dichlorophenyl)propionamidine.

* * * * *

UNITED STATES PATENT AND TRADEMARK OFFICE
CERTIFICATE OF CORRECTION

PATENT NO. : 4,093,655
DATED : June 6, 1978
INVENTOR(S) : George A. Miller and Marvin H. Fleischfresser It is certified that error appears in the above-identified patent and that said Letters Patent are hereby corrected as shown below:

<u>Table 1, Ex. No. 8, under heading Amidine</u> - name should read
-- N-n-octyl-N'-2,3-dichlorophenyl)propionamide --.

<u>Table II, Amidine Example No. 6</u> - results should read
-- canarygrass - dash; Dallisgrass - 100; cattail - 70; rice - 60; barnyardgrass - 100; umbrella sedge - 95 and coffeweed - 100 --.

Signed and Sealed this

Thirtieth Day of January 1979

[SEAL]

Attest:

RUTH C. MASON
Attesting Officer

DONALD W. BANNER
Commissioner of Patents and Trademarks